United States Patent
Schrof et al.

(10) Patent No.: US 6,278,518 B1
(45) Date of Patent: Aug. 21, 2001

(54) CENTRIFUGING PROCESS FOR SAMPLE CHARACTERIZATION

(75) Inventors: Wolfgang Schrof, Neuleiningen; Peter Rossmanith; Walter Mächtle, both of Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/109,765

(22) Filed: Jul. 6, 1998

(30) Foreign Application Priority Data

Jul. 9, 1997 (DE) .............................................. 197 29 352

(51) Int. Cl.$^7$ .................................................. G01N 21/51
(52) U.S. Cl. ........................... 356/318; 356/36; 73/61.66; 73/32 R
(58) Field of Search ................... 356/318, 36; 73/61.66, 73/61.68, 64.56, 863, 866, 864.81, 32 R, 865.3, 61.69, 61.48; 436/177, 171; 422/72; 494/10

(56) References Cited

U.S. PATENT DOCUMENTS

| | | | |
|---|---|---|---|
| 3,610,757 | * 10/1971 | Van Valkenburg et al. | 356/36 |
| 4,448,524 | * 5/1984 | Brus et al. | 356/36 |
| 4,886,358 | * 12/1989 | Pellenbarg et al. | 356/36 X |
| 5,061,075 | * 10/1991 | Alfano et al. | 356/318 X |
| 5,607,643 | * 3/1997 | Xiaoming et al. | 356/301 X |
| 5,733,507 | * 3/1998 | Zakim | 422/101 |
| 5,751,415 | * 5/1998 | Smith et al. | 356/301 |

OTHER PUBLICATIONS

Machtle et al., "Analysis of Polymer Dispersions . . . " in Harding et al., *Analytical Ultracentrifugation in Biochem. and Polymer Science*, Royal Society of Chemistry, Cambridge, England 1992, Chapter 10., pp. 147–175, Month Not Given.

* cited by examiner

Primary Examiner—Thomas P. Noland
(74) Attorney, Agent, or Firm—Keil & Weinkauf

(57) ABSTRACT

A process for characterizing at least one sample comprising at least one substance ($S_i$), in which at least one substance ($S_i$) in the sample is identified and in which at least one quantity ($G_{ji}$) which characterizes a substance ($S_i$) in the sample is determined, at least the following process steps being carried out successively or simultaneously in an analytical centrifuging device:

a) centrifuging the sample in an analytical centrifuge,
b) exposing the sample to monochromatic light, preferably laser light,
c) detecting light scattered by the sample,
d) identifying at least one substance ($S_i$) by a spectral evaluation of the inelastically scattered fraction of the scattered light which was detected in step c), e.g. by means of Raman scattering, and
e) determining at least one quantity ($G_{ji}$) for a substance ($S_i$) by evaluating the state of the sample which it has entered as a consequence of the centrifuging in step a).

10 Claims, 1 Drawing Sheet

CENTRIFUGING PROCESS FOR SAMPLE CHARACTERIZATION

BACKGROUND OF THE INVENTION (a) Field of the Invention

The present invention relates to a process and a device for characterizing a sample which has at least one substance dissolved or dispersed in it, by a combination of analytical centrifuging and spectral evaluation of the inelastically scattered fraction of the scattered light emitted by the at least one substance. In particular, the invention relates to a process and a device for determining quantities characteristic of dissolved or dispersed substances in the form of particles, for example the density, molecular weight, molecular weight distribution and particle size distribution of the substances in the form of particles, providing extra information regarding the structure of the particles. In the context of the invention, "particle" is used to denote the investigated substances/materials in the form of dissolved and/or dispersed particles, this including substances both with low molecular weight and with high molecular weight.

(b) Description of Related Art

One known process for determining the characteristic quantities mentioned above is analytical centrifugation, although owing to the size of the substances which are generally to be investigated, in the form of particles, use is predominantly made of analytical ultracentrifugation. Moreover, the present application is to be understood such that other analytical centrifuges, for example a disc centrifuge, that is to say centrifuges in which only a comparatively low speed of rotation can be obtained, may also be used in the context of the process according to the invention. Nevertheless, the present invention will be explained below with reference to analytical centrifuges, and this being the case it should be noted that the term "ultracentrifuge" used in the context of the present invention always means an analytical ultracentrifuge (AUC).

In an ultracentrifuge, that is to say a very fast centrifuge with which speeds of 60,000 rpm or more can be obtained, it is possible to separate (fractionate) mixtures of substances which have different density and/or size. This being the case, ultracentrifuges can be used in a variety of ways, an overview being found, for example, in an article by W. Mächtle "*Analysis of Polymer Dispersions with an Eight-Cell-AUC-Multiplexer: High Resolution Particle Size Distribution and Density Gradient Techniques*" in S. E. Harding et al. (Ed.) "Analytical Ultracentrifugation in Biochemistry and Polymer Science", Royal Society of Chemistry, Cambridge England 1992, Ch. 10.

The most important AUC measurement techniques are the sedimentation (S) run which fractionates the particles according to size, that is to say according to their molecular weight distribution or particle size distribution, the equilibrium run with which it is possible to determine the weight average of the molecular weight of the particles, and the density gradient (DG) run which fractionates according to density, that is to say according to chemical nonuniformity, number of components, degree of grafting, etc.

As indicated above, centrifuging can take place in a variety of ways:

1. Sedimentation run (S run)

During the S run, the sample(s) to be analyzed is or are subjected to a constant or increasing speed of rotation, starting from about 600 rpm and increasing to about 60,000 rpm. Since the sedimentation rate of the particles inside the sample is proportional to the square of the rotational speed, particles of a given size sediment 10,000 times faster when the rotational speed is increased from, for example, 600 to 60,000 rpm. Through measurement of a quantity, for example absorption, characteristic of the particles contained in the sample, it is possible to observe the kinetics of the particle sedimentation during an S run of this type. The speed at which the particles move to the bottom of the sample holder depends on their diameter. An S run therefore makes it possible to draw direct conclusions regarding the particle size and its distribution within a sample, since determination of a quantity characteristic of the sample at time T over the entire sample gives access to the "true" state of the sample in terms of the distribution of the particles within it. To this end, it is necessary to know particular auxiliary quantities, for example the particle density, the absorption coefficient or the specific refractive index increment.

A particularly useful way of separating a sample which contains particles with low and high molecular weights is to carry out a layering run using layering cells, as can be obtained from Messrs. Beckman for example. In addition to at least one analysis chamber, which contains the sample, a layering cell of this type contains at least one store chamber which contains solvent. During the ultracentrifuging run, this solvent is then released as a result of the fact that, above a certain ultracentrifuge speed, the partition between the chamber containing the sample and the store chamber for the solvent is removed, and the solvent can thus enter the chamber containing the sample.

During the layering run, the ultracentrifuge is thus firstly started up, then above a certain speed the solvent in the store chamber enters the sample chamber and forms a layer on the solution which it contains. During this run, the large particles sediment in the direction of gravity, while the small particles, which are incapable of sedimenting on account of their small size, remain at the interface between the sample solution and the solvent forming a layer. The effect of the presence of the extra solvent is that the band attributable to these small particles broadens since the particles partly diffuse into the extra solvent.

This method is extremely useful for separating samples which contain both small and large particles together.

2. Equilibrium run

In an equilibrium run, the weight average of the molecular weight Mw of particles can be determined. To do this, samples with different particle concentration c are centrifuged at the same time at one rotor speed until steady state conditions are reached. The relevant concentration distribution is determined from the radial concentration profile of the particles under steady state conditions within the measuring cell, and using the abovementioned auxiliary quantities which need to be determined separately, an apparent molecular weight $M_c$ is calculated. Plotting $1/M_c$ against c and extrapolating to c=0 gives $M_W$. Using this method, it is possible to register particles with a weight average of the molecular weight of about 300 to $1 \times 10^8$ g/mol. Optical techniques involving an interference or schlieren method are generally used for determining the radial concentration profile in the individual samples. When schlieren methods are used, however, all other things being equal, the Z average of the molecular weight Mz is determined instead of $M_W$. By evaluating $M_Z$ and $M_W$ it is possible to draw conclusions regarding the molecular weight distribution and therefore the nonuniformity of a sample, for example a polymer.

3. Density gradient run (DG run)

A further option for ultracentrifuging involves mixing two solvents having different densities with the particles to be examined, and then centrifuging this mixture. The two differently dense solvents then form a density gradient in the sample, in which the particles are ordered according to their own density, which is to say they will stay at a fixed radial position where the density of the solvent mixture surrounding them corresponds to their own density. This method thus makes it possible to separate particles from one another according to their density, and thus according to their chemical nature. For example, polymer mixtures can in this way be broken down into their individual components. It is in this way possible, for example, to check that a block copolymerization has been brought successfully to its conclusion, or to determine the average and distribution of the degree of grafting in a graft dispersion.

However, although ultracentrifuging is an elegant way of fractionating samples according to molecular weight, particle size and density of the particles which they contain, this method does not in principle allow chemical identification of the fractions.

For this reason, ultracentrifuging has in the past been coupled with determination of absorption and fluorescence spectra during the ultracentrifuging run, in order to make it possible to draw conclusions regarding the "chemistry" of the particles contained in the sample. However, in particular if the particles contained in the sample are organic in nature, these methods provide only minor advantages, since the (usually) organic materials exhibit no, or at best very similar, UV/VIS absorption and/or fluorescence. Further, it is often necessary when recording fluorescence spectra to correspondingly label the particles to be examined, and this generally entails an additional working step.

SUMMARY OF THE INVENTION

The object of the present invention is accordingly to provide an ultracentrifuging process with which it is possible, in a simple and accurate fashion, to identify various particles in a sample during or after their separation in a centrifuge.

This object is achieved by the ultracentrifuging process according to the invention. This process represents a process for characterizing at least one sample comprising at least one substance ($S_i$), in which at least one substance ($S_i$) in the sample is identified and at least one quantity ($G_{ji}$) which characterizes a substance ($S_i$) in the sample is determined. This being the case, according to the invention, at least the following process steps are carried out successively or simultaneously in an analytical centrifuging device:

a) centrifuging the sample in an analytical centrifuge, preferably an analytical centrifuge. In this context, an analytical ultracentrifuge is a centrifuge which rotates fast enough to separate even materials with relatively minor differences in density. In the scope of the invention, the duration and conditions of the centrifuging, for example the speed, the time profile of the speed, the duration of the run or the sample geometry may be tailored to the relevant working requirements. Likewise, the structure, for example the number of sample chambers and the way in which they are arranged, of the ultracentrifuge which is used may be tailored to the relevant requirements. Further, the centrifugation may, depending on the separation problem, be carried out as a sedimentation, density gradient or equilibrium run, as respectively defined above.

b) Exposing the sample to monochromatic light, preferably laser light. This light is scattered by the sample.

The frequency of the applied monochromatic light is chosen such that resonant amplification of the scattered light or fractions of the scattered light takes place. In this way, resonance can be created in the Raman effect discussed in the next step, and in many cases this is the only way in which it is possible to detect substances present only at trace levels.

c) This light scattered by the sample is detected. To do this, it is possible to use any optical detection systems which permit detection according to spectroscopic bands, for example photomultipliers, photodiodes, two-dimensional detectors (CCD photodiodes, etc.) in conjunction with spectrographs, gratings, prisms and color or interference filters. In particular, all scattered light fractions should be picked up which have a wavelength shift relative to the applied light, and are thus due to inelastic light scattering from the sample, for example molecular or lattice modes. This wavelength shift is generally referred to as the Raman effect or Brillouin effect.

Preferably, the light back-scattered from the sample is detected. This makes it possible to examine even samples which are opaque or weakly transparent, in particular optically thick polymer samples.

d) Identifying at least one substance ($S_i$) by a spectral evaluation of the inelastically scattered fraction of the scattered light which was detected in step c), i.e. the Raman scattered light. In this case, Raman spectroscopy is thus used to identify at least one substance ($S_i$) in the sample, that is to determine its chemical composition. A number of Raman spectroscopy methods which are useful for the invention have been described in B. Schrader, Infrared and Raman Spectroscopy, Weinheim, 1995 and L. Markwort, B. Kip, E. Da Silva, B. Roussel, Applied Spectroscopy, 49 (1995) 1411. In this context, it is not absolutely necessary to determine the full chemical composition of the relevant substance. In many cases, it is sufficient for substances in a mixture to be discriminated qualitatively from one another in a sample. Nevertheless, it is in certain cases also necessary or desirable to determine not only the chemical composition of a substance in a sample, but also its bonding state on the basis of the measured molecular modes. A particular advantage with Raman spectroscopy is that it is not sensitive to polar compounds, and this permits measurements in an aqueous medium without the Raman spectra of other components of the samples having the water bands superposed on them. It is further possible, using new high-sensitivity spectrometers which work primarily with back-scattering, for example a combination of notch filters, simple spectrographs, CCD arrays and high-efficiency imaging optics, etc., for the measuring times to be shortened to seconds. Combining Raman spectroscopy with microscopes and fibre optics allows measurements with $\mu m$ spatial resolution, and also for the measuring head and spectrometer to be placed at different locations, a point which will be dealt with in further detail below.

Further, the identification of a substance in the sample may also take place through evaluation of the intensity of the elastic scattered light fraction. The spectrum or intensity of fluorescent light emitted by the sample may also be used supplementarily, in order to determine the identity of substances in the sample. In this case, the determination of the fluorescence and light scattering may be determined in both the forward and back directions.

For determining absorption, use is made of a dual beam spectrograph especially tailored to the equipment set-up in the ultracentrifuge, in which one beam of the applied monochromatic light is directed into the sample, and a parallel beam of the same light is directed into the corresponding pure solvent.

The refractive index may be determined using an interference or schlieren optical method.

Of course, the process discussed here, or the device used in this context, may be coupled with a corresponding database of, for example Raman spectra, and thus permit fast identification even of an unknown substance in the sample. In particular, this makes it possible for the process described here to be used for routine analysis of samples, in particular polymer dispersions. Examples which may be mentioned include, in particular: styrene, butadiene, acrylate, acrylonitrile, amide, etc., homo- and copolymers, and inorganic or organic pigments.

Further, the process according to the invention is particularly useful for examining samples of unknown composition and the distribution of known substances within a sample.

e) Determining at least one quantity ($G_{ji}$) for a substance ($S_i$) by evaluating the state of the sample which it has entered as a consequence of the centrifuging in step a). In this process step, the characteristic quantities of a substance ($S_i$) which are determined are those which can in any case be determined using ultracentrifuging processes, cf. W. Mächtle, S. Harding, AUC in Biochemistry and Polymer Science, Cambridge, 1991; W. Mächtle, Angewandte Makromolekulare Chemie, 162 (1988) 35; W. Mächtle, Colloid and Polymer Science, 262 (1984) 270. Preferably, the quantities ($G_{ji}$) determined are the density or the sedimentation rate or sedimentation coefficient of a substance ($S_i$) in the sample.

From the characteristic quantities determined in this process step, it is then possible in an additional evaluation step to determine the desired values, for example molecular weight distribution or particle size distribution.

Preferably, a difference in the refractive index at various points in the sample is used to determine the quantity ($G_{ji}$) of a substance ($S_i$). It is in this way, for example, possible for domains of substances in the sample to be determined after the ultracentrifuging. Under certain circumstances, the substance of interest must first of all be found in the sample, because it is not optically distinguishable from the rest of the sample, but is separated by the ultracentrifuging in terms of density, size, etc. and subsequently it is possible for the individual fractions to be examined spectroscopically. This is often the case with samples of a mixture of polymers having different structures but the same basic chemical composition.

The measurement of the differences in refractive index along the sample may in this case be carried out using any known process for determining the refractive index of a sample. As a rule, a separate light source is provided for these measurements, in addition to the monochromatic light source mentioned in step b). It is, however, also conceivable to deviate a fraction of the monochromatic light for this case, so that only one light source is required. In the context of the invention, it is not absolutely necessary to determine absolute values of the refractive index. In many cases, it is sufficient to determine variations in refractive index merely qualitatively, in order for example to recognize a domain of a substance in the sample by means of a sudden jump in the refractive index. This substance can then be identified using Raman spectroscopy, so that the variations in the refractive index are used merely as a probe.

A preferred process is one in which use is made of an optical system which shifts the focal point of the monochromatic light applied in step b) inside the sample, for example confocal optical imaging in which moving the source to and fro makes it possible to adjust the observed depth segment within a sample. In this case, it is possible to achieve an accuracy of about 1 to 3 μm in terms of the focal point which is set, that is to say of the desired depth segment. The depth sharpness can be set by using a diaphragm or an optical fiber with appropriate internal diameter, which is to say this method makes it possible to scan a sample both vertically, i.e. in the direction of the light beam (depth profile) and radially, i.e. in the direction of gravity. If fairly large lateral regions are to be observed, then it is further possible in the context of the present invention to translate the entire optical system, for example using a traveling table or a piezo mechanical device. Using arrangements of this type is, for example, advantageous if sample chambers are used in the ultracentrifuge which are divided radially and/or vertically into a plurality of parallel subchambers. This makes it possible to scan a plurality of samples at the same time during a single ultracentrifuging operation.

Shifting the focal point for the incidence cone of the monochromatic light, as well as a corresponding shift in the observation cone for detecting the scattered light, also allows the successive examination of a plurality of samples, which are contained in parallel chambers within a cell, without providing separate optical systems for each chamber. In general, the preferred process makes it possible to scan a sample locally.

A further preferred process is one in which it is possible to shift the point of application of the monochromatic light in step b) and, in step c), shift the point of detection of the scattered light along the sample. This makes it possible to examine the sample during the centrifuging using a single Raman spectroscopy system, since this is simply moved to and fro along the sample. Nevertheless, depending on the intended purpose, it is also possible to measure the sample statically at a single point, and for example to observe the motion of the particles through this point.

The present invention can be applied particularly advantageously using fiber optics. For example, the monochromatic light used to generate the scattered light can be applied to the sample using an optical fiber. The detection may then likewise take place using optical fibers. This makes it possible to arrange the elaborate Raman technology in a different place from the ultracentrifuge. Both parts of the measuring set-up may for example be in separate laboratories, and may be connected using fiber optics and, where appropriate, a control system for the abovementioned preferred movement of the light source and the Raman detector along the sample.

For characterizing a plurality of samples at the same time, with a plurality of samples being centrifuged simultaneously using a multichamber rotor and simultaneously examined using Raman spectroscopy, the process according to the invention may be carried out as follows.

Light pulses, for example from a pulsed laser or a modulated continuous wave laser are focused on the individual cells in a rotor, for example a 4 or 8 hole rotor, using optical triggering. The Raman light detected under back-scattering conditions is analyzed in a spectrometer.

Using a two-dimensional detector, for example a CCD array, makes it possible on the one hand to detect the back-scattering from the individual samples (for example in horizontal lines) and, on the other hand, to allocate to specific yet different chambers (for example in vertical lines)

using, for example, a tilting mirror driven synchronously, for example by an electrically controlled suspension, or piezo-translators or acousto- and electro-optical beam guide systems. This permits simultaneous characterization of the samples within the chambers.

The measurement may, of course, also be carried out sequentially, for example with the AUC running for a sufficiently long time, in which case it is not necessary to have the extra optical imaging system.

With this measuring arrangement, the process according to the invention is very useful for routine analysis.

The present invention also provides a device for characterizing at least one sample which contains at least one substance ($S_i$). According to the invention, this device has at least the following interacting components:
an analytical centrifuging device having at least one chamber for holding the sample,
a device for exposing the sample to monochromatic light and for detecting light scattered by the sample, and
a device for determining a quantity $G_{ji}$ which characterizes the substance $S_i$.

This device can be used to carry out the process according to the invention presented above. It may also be supplemented by further elements which are necessary or useful for carrying out the preferred or advantageous variants of the process according to the invention which have been presented above.

BRIEF DESCRIPTION OF THE DRAWINGS

The present invention will be described below with reference to FIGS. 1 and 2, in which.

DETAILED DESCRIPTION

Figure 1:
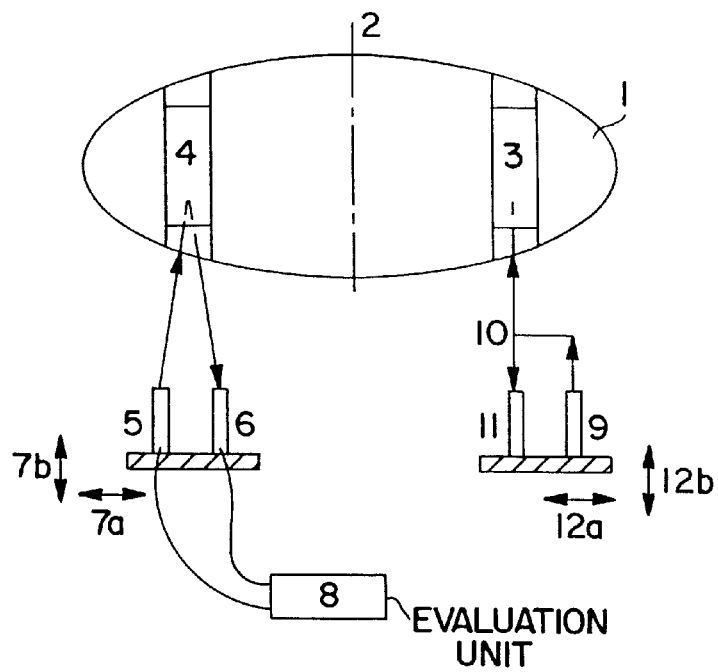
FIG. 1: shows an embodiment of a sample characterization device according to the invention.

FIG. 1 shows a schematic representation of a sample characterization device according to the invention. It contains a rotor 1 with an axis of rotation 2 and a cell, having at least one chamber which is intended to hold a sample and is located in a bore in the rotor (3, 4), a laser light source 5, which may or may not have an optical imaging system and can apply light to the cell 4, and a detection system 6 which can record back-scattered light from the sample chamber 4 with spectral discrimination. Further, a light source 9 may be projected onto the cell 3 using a notch filter 10. The back-scattered light passes through the notch filter 10 and is spectrally analyzed in the detection system 11. The light source 5, 9 and the detection system 6, 11, or its optical imaging system, may be fitted on separate supports or on a common support (not shown). In both arrangements, it is possible for them to be moved synchronously along the arrows 7a or 12a, radially, and along the arrows 7b or 12b, vertically. It is therefore possible to scan the cells 3, 4 in the radial direction 7a, 12a and vertical direction 7b, 12b.

While the rotor 1 is turning about the axis of rotation 2, the light source 5 can apply monochromatic light to the cell 4 just when it is moving past it in the course of a revolution. The elastically and inelastically scattered light is registered under a back-scattering geometry by the detection system 6, 11 or its optical imaging system. The detection system forwards the recorded values to the evaluation unit 8 which undertakes the evaluation. The characteristic quantities of a substance which has been found and identified, for example density, sedimentation rate, sedimentation coefficient, molecular weight distribution or particle size distribution, can be determined with the usual processes (not represented or described here) for conventional ultracentrifuges.

Figure 2:
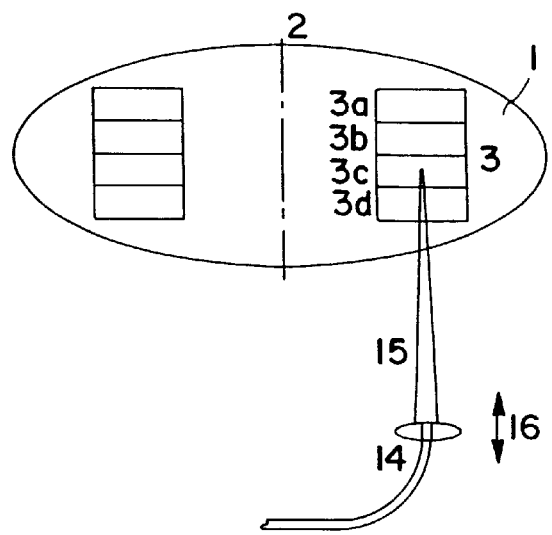
FIG. 2: shows a detail of a preferred sample characterization device according to the invention

FIG. 2 shows a detail of a preferred embodiment of the sample characterization device according to the invention. A cell 3 inside the rotor 1 is here divided in the vertical direction, parallel to the axis of rotation 2, into four chambers 3a to 3d. It is therefore possible to measure a plurality of samples simultaneously and under identical conditions. According to the invention, a light source 14 is used in a focal optical configuration with a focal point 15, it being possible for the focal point 15 to be shifted inside the cell 3 between the subchambers 3a to 3d, vertically along the arrow 16, and where appropriate radially with respect to it. It is therefore possible for all four subchambers to be examined successively without using separate optical systems. This is beneficial, above all, in the case of a light source 14 which applies monochromatic light to the sample for Raman scattering, and for a corresponding detection system.

We claim:

1. A process for characterizing at least one sample comprising at least one substance ($S_i$), in which at least one substance ($S_i$) in the sample is identified and in which at least one quantity ($G_{ji}$) which characterizes a substance ($S_i$) in the sample is determined, wherein, at least the following process steps are carried out successively or simultaneously in an analytical centrifuging device:

a) centrifuging the sample in an analytical centrifuge,
   b) exposing the sample to monochromatic light,
   c) detecting light scattered by the sample,
   d) identifying at least one substance ($S_i$) by a spectral evaluation of the inelastically scattered fraction of the scattered light which was detected in step c), and
   e) determining at least one quantity ($G_{ji}$) for a substance ($S_i$) by evaluating the state of the sample which it has entered as a consequence of the centrifuging in step a).

2. The process as claimed in claim 1, wherein the density of a substance ($S_i$) in the sample is determined in step e) as the quantity ($G_{ji}$).

3. The process as claimed in claim 1, wherein the sedimentation rate of a substance ($S_i$) in the sample is determined in step e) as the quantity ($G_{ji}$).

4. The process as claimed in claim 1, wherein a difference in the refractive index at various points in the sample is used for the determination in step e).

5. The process as claimed in claim 1, wherein an evaluation of the intensity of the elastic scattered-light fraction or the spectrum or the intensity of fluorescent light emitted by the sample, or a combination of two or more of these, is in addition carried out in step d) for the identification.

6. The process as claimed in claim 1, wherein the back-scattered light is detected in step c).

7. The process as claimed in claim 1, wherein an optical system, which shifts the focal point of the light applied in step b) within the sample, is used for the detection according to step c).

8. The process as claimed in claim 1, wherein use is made of a device which, in step b), shifts the point of application of the monochromatic light and, in step c), shifts the point of detection of the scattered light along the sample.

9. The process as claimed in claim 1, wherein the frequency of the applied light is chosen in step b) such that resonant amplification of the scattered light or fractions of the scattered light takes place.

10. A process as claimed in claim 1, wherein the sample is exposed to laser light in step b).

* * * * *